United States Patent
Sugiyama et al.

(10) Patent No.: US 7,910,357 B2
(45) Date of Patent: Mar. 22, 2011

(54) CORRECTION METHOD FOR THE DISTRIBUTION OF QUANTITY OF LIGHT AND BIOCHIP-READER

(75) Inventors: Yumiko Sugiyama, Musashino (JP); Takeo Tanaami, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 1013 days.

(21) Appl. No.: 11/707,133

(22) Filed: Feb. 16, 2007

(65) Prior Publication Data

US 2007/0141623 A1    Jun. 21, 2007

Related U.S. Application Data

(62) Division of application No. 10/931,962, filed on Sep. 2, 2004, now Pat. No. 7,666,663.

(30) Foreign Application Priority Data

Dec. 24, 2003 (JP) ................... 2003-426153

(51) Int. Cl.
- C12M 1/34 (2006.01)
- C12M 3/00 (2006.01)
- C12M 1/00 (2006.01)
- G01N 21/64 (2006.01)
- G01N 21/66 (2006.01)

(52) U.S. Cl. .............. 435/288.7; 435/283.1; 435/287.1; 422/82.07; 422/82.08

(58) Field of Classification Search .............. 435/6, 7.1, 435/91.1, 283.1, 287.1, 287.2, 288.7; 422/50, 422/68.1, 87.07, 87.08

See application file for complete search history.

(56) References Cited

U.S. PATENT DOCUMENTS

| 5,799,773 A * | 9/1998 | Heffelfinger et al. ......... 204/461 |
| 2003/0030797 A1 | 2/2003 | Palladino et al. |
| 2003/0105195 A1 | 6/2003 | Holcomb et al. |

FOREIGN PATENT DOCUMENTS

| JP | 2003-28799 | 1/2003 |
| JP | 2004-101354 | 2/2004 |
| WO | WO 01/55964 A2 | 8/2001 |
| WO | WO 01-59503 | 8/2001 |
| WO | WO 03/00300 A1 | 1/2003 |
| WO | WO 2004-023117 | 3/2004 |

OTHER PUBLICATIONS

The definition for "pixel". Printed on Dec. 4, 2009.*
Y. Zhai et al. "Quantitative determination of the proportion of microtubule polymer present during the mitosis-interphase transition", Journal of Cell Science 107, pp. 881-890 (1984).

* cited by examiner

Primary Examiner — Frank W Lu
(74) Attorney, Agent, or Firm — Westerman, Hattori, Daniels & Adrian, LLP

(57) ABSTRACT

The present invention is characterized by the following points:
In a biochip reader used for reading a measurement sample image by light beam irradiation, a correction method for the distribution of quantity of light which is devised to remove the influence of shading for the whole image and such a biochip reader can be realized by correcting non-uniformity in said quantity of light in light beam irradiation by dividing the quantities of light of pixels in a measured image obtained from the measurement of a measurement sample by a distribution of quantity of light in an image obtained from the measurement of a uniform fluorescent plate that presents a uniform fluorescent light distribution, the positions of pixels in the measured image being correspondent to those in the image obtained through the above uniform fluorescent plate measurement.

4 Claims, 4 Drawing Sheets

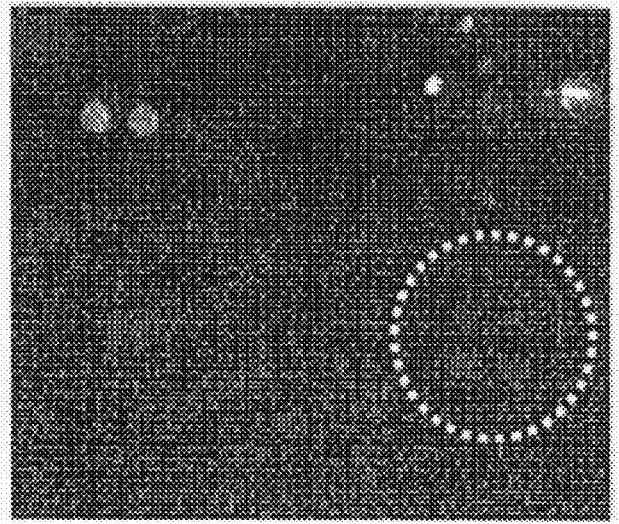
FIG.2A — Uniform fluorescent plate
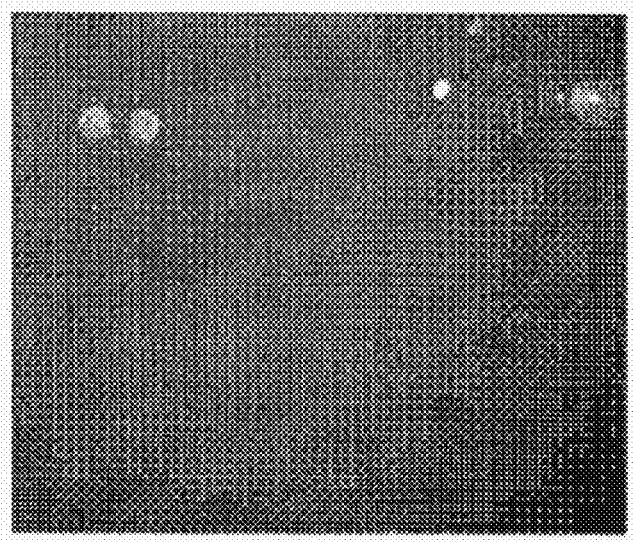
FIG.2B — Sample:Before correction
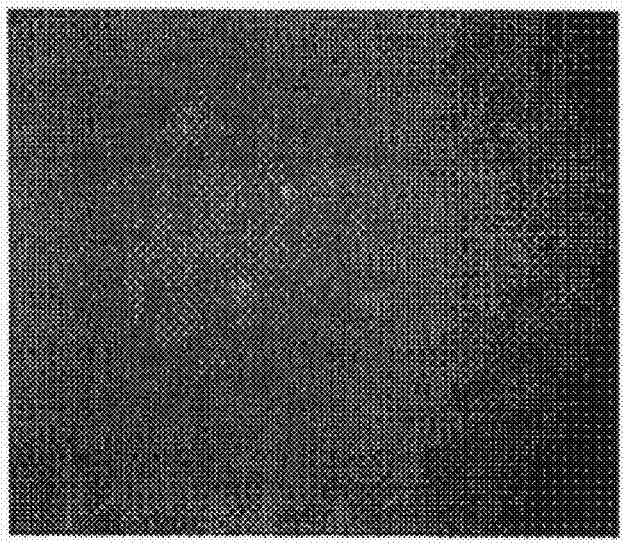
FIG.2C — Sample:After correction Correction distribution

CORRECTION METHOD FOR THE DISTRIBUTION OF QUANTITY OF LIGHT AND BIOCHIP-READER

This application is a divisional of application Ser. No. 10/931,962, filed on Sep. 2, 2004, now U.S. Pat. No. 7,666,663 B2.

BACKGROUND OF THE INVENTION

1. Field of the Invention

The present invention relates to a biochip reader and also to a method for correcting the influence of intensity distribution (shading) of a light source (excitation light). Specifically, the influence of this shading is large in the scan-less type biochip reader in which a wide biochip range is measured simultaneously with a plurality of light beams.

2. Description of the Prior Art

This kind of scan-less type biochip reader is well known from the past (for example, refer to Patent Document 1). FIG. 1 is a configuration drawing indicating the essential part of an example of the scan-less type biochip reader described in Patent Document 1.

In FIG. 1, laser light (excitation light) emitted from a light source becomes parallel light and is incident to microlens array 1. Microlens array 1 is an arrangement of a plurality of microlenses (ML) and excitation light converged respectively by each microlens (ML) irradiates measurement sample 3 after transmitting dichroic mirror 2. Measurement sample 3 is constructed so that a plurality of cells(sites) is arranged in a two-dimensional manner and a sample is poured in each cell(site).

Fluorescent light from each sample is reflected by dichroic mirror 2 and is incident to lens 5 via barrier filter 4. Barrier filter 4 has the effect of acting to transmit fluorescent light from measurement sample 3 but to attenuate the excitation light reflected by measurement sample 3, and is used to eliminate the background light of a sample image. A sample image focused and formed by lens 5 is captured by camera 6.

According to such a configuration, a plurality of cells (sites) on a biochip can be measured at the same time with a scan-less method in which excitation light is not scanned.

[Patent Document 1]
Gazette for Japanese Laid-open Patent Application No. 2003-28799 (p. 6, FIG. 13)

However, in such conventional biochip readers, the distribution of excitation light intensity becomes the distribution of excitation light intensity on the measurement plane of a biochip without change and thus excitation light intensity is different at each site even on the same chip. Accordingly, conventional biochip readers have the following problems:

(1) There are portions on a biochip where excitation light is strong and portions on the same biochip where excitation light is weak. This affects the amount of fluorescent light emission. In particular, differences between these strong and weak light intensities are extremely large for scan-less type readers.

(2) If the quantities of light are simply corrected using a certain factor, they become unknown in the case where the absolute quantity of light calibration system using a power meter traceable to national standards is used.

(3) If the quantities of light are simply corrected using a certain factor, pixels may be easily saturated or the tones over the whole pixels of images may be lowered to the span.

SUMMARY OF THE INVENTION

The objective of the present invention is to solve such problems and thus to offer a correction method for the distribution of quantity of light, which removes the influence of shading of the whole image by measuring a reference quantity of light distribution image of the excitation light using a uniform fluorescent plate that presents a uniform fluorescent light distribution and by dividing the measured sample image by the aforementioned reference quantity of light distribution image to correct non-uniformity of a quantity of light, and to offer a biochip reader using the above described method.

BRIEF DESCRIPTION OF DRAWINGS

FIG. 1 is a configuration drawing indicating the essential part of an example of conventional scan-less type biochip readers.

[FIG. 2]
FIG. 2 shows FIG. 2A, FIG. 2B and FIG. 2C are drawings for illustrating a correction method for the distribution of quantity of light concerning the present invention.

[FIG. 3]
FIG. 3 shows

FIG. 4 is a configuration drawing indicating the essential part of an embodiment of a biochip reader using the method of the present invention.

DESCRIPTION OF THE PREFERRED EMBODIMENTS

The present invention will be described below in detail using drawings. The procedure for the correction method for the distribution of quantity of light is as shown below. A biochip reader may be either the scan-less type or a scanning type.

(1) First, a uniform fluorescent plate is prepared, that presents a uniform fluorescent light distribution in a range having an area equivalent to a measurement area for a measurement sample. Then a fluorescent image of this uniform fluorescent plate, that is, the reference quantity of light distribution image "a" is measured by irradiating excitation light using a biochip reader. The value (light intensity) of each pixel in this case is given as "$a_i$" ("i" shows the number of pixels and so takes a value 1 to n).

(2) The average tone "$a_{Ave}$" of the above obtained reference quantity of light distribution image "a" is determined, then the light source intensity correction image "a'" is determined by dividing the values of each pixel by this average tone "$a_{Ave}$" [the values of each pixel are represented by "$a'_i$" (i=1 to n)].

This enables a light source intensity correction image, in which the tone of the reference quantity of light distribution image "a" is normalized to 1 and the total energy value is made unchanged as shown in FIG. 2A, to be obtained. In addition, FIG. 2 shows images measured with a scanning type biochip reader.

(3) A measurement sample is measured using a light source of the same intensity distribution in the same biochip reader as mentioned before to obtain a measurement sample image "b" [values of each pixel are "$b_i$" (i=1 to n) as shown in FIG. 2B.

(4) Next, as shown in equation (1), a corrected sample image "c" [values of each pixel are "$c_i$" (i =1 to n)] is determined by dividing the measurement sample image "b" by the above described light source intensity correction image "a'".

$$c_i = b_i \div a'_i \quad (1)$$

According to this correction method, the following effects are obtained:
(1) Normalization of the tone of the light source intensity correction image to 1
    gives no change in the total energy, that is, the total quantity of light energy is maintained, and
    prevents the values of pixels from taking extremely large or small values.
(2) Fluorescent images of sites, which cannot be seen in FIG. 2B due to the lack of uniformity in the distribution of the quantity of light for the light source, become visible by performing correction as shown in the circle at the lower left of FIG. 2C. In other words, highly sensitive measurements are made possible.

Figure 3A:
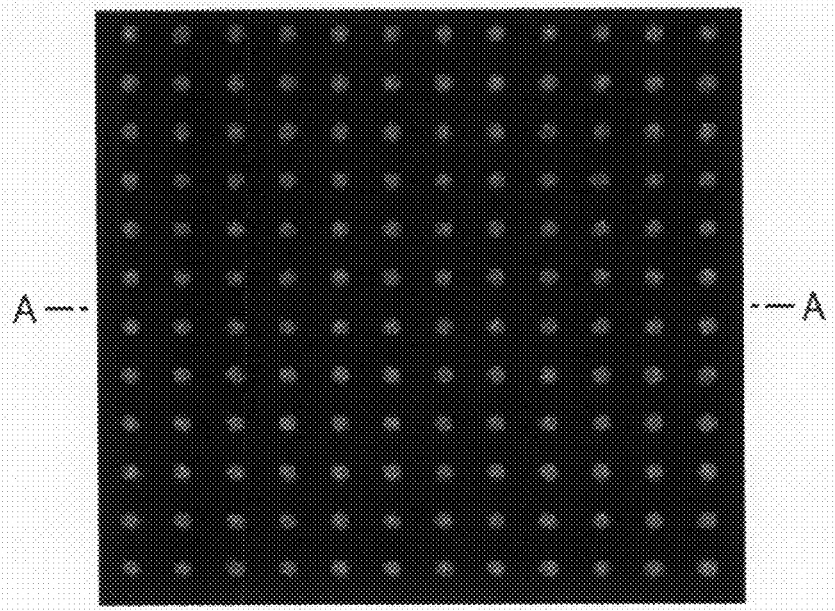
FIG. 3A and FIG. 3B are drawings for illustrating the distribution of light intensity and the distribution of quantity of light for a scan-less type reader.
Figure 3B:
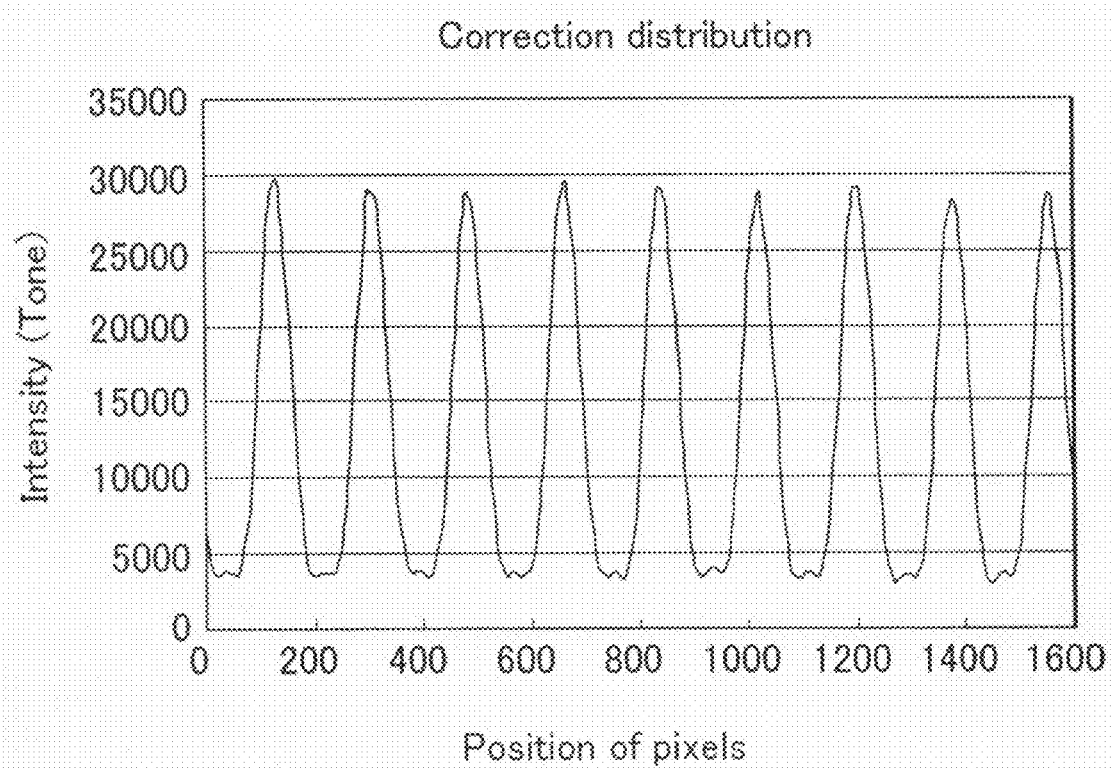

Further, if a biochip reader is of the scan-less type which does not scan a light beam, a far more non-uniform intensity distribution than that in the image shown in FIG. 2B is generated as shown in FIG. 3A. However, the distribution can also be corrected using a similar technique. A corrected light intensity distribution of the sites on the A-A line shown in FIG. 3A is indicated in FIG. 3B.

If a camera for capturing images or the like has an offset x, the value for offset should be subtracted from values of each pixel in advance before performing division as shown in equation (2).

$$c_i = (b_i - x) \div \{(a_i - x) \div (a_{Ave} - x)\} \quad (2)$$

Figure 1:
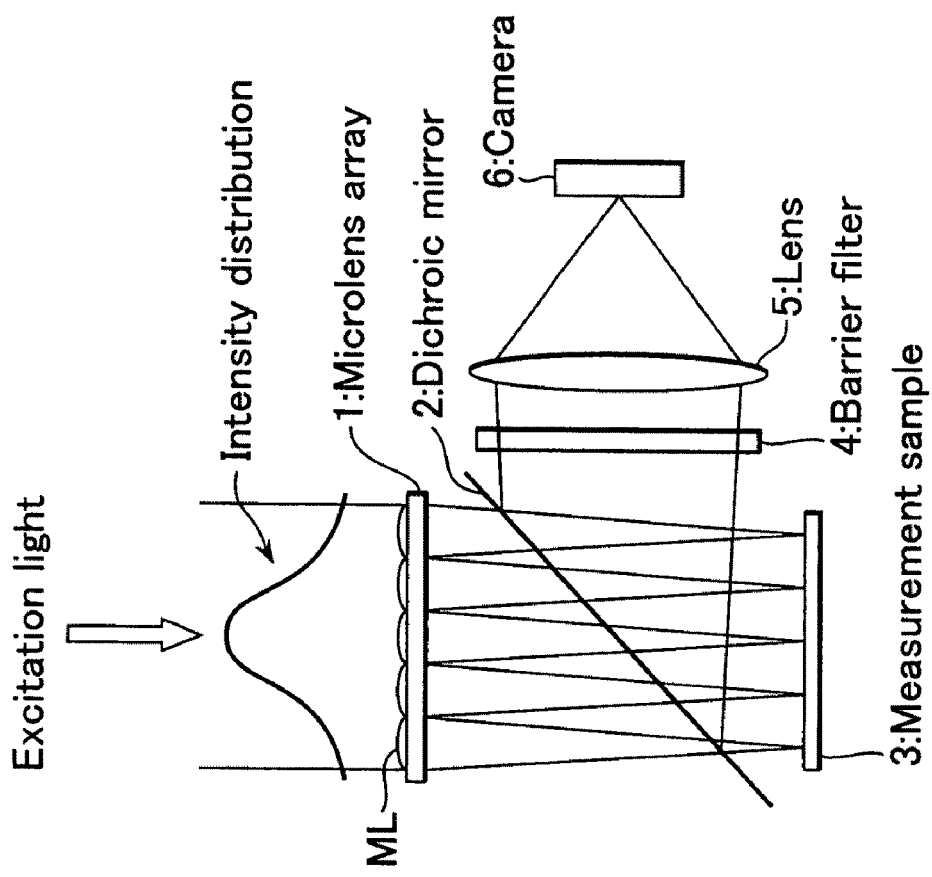
[FIG. 1]
Figure 4:
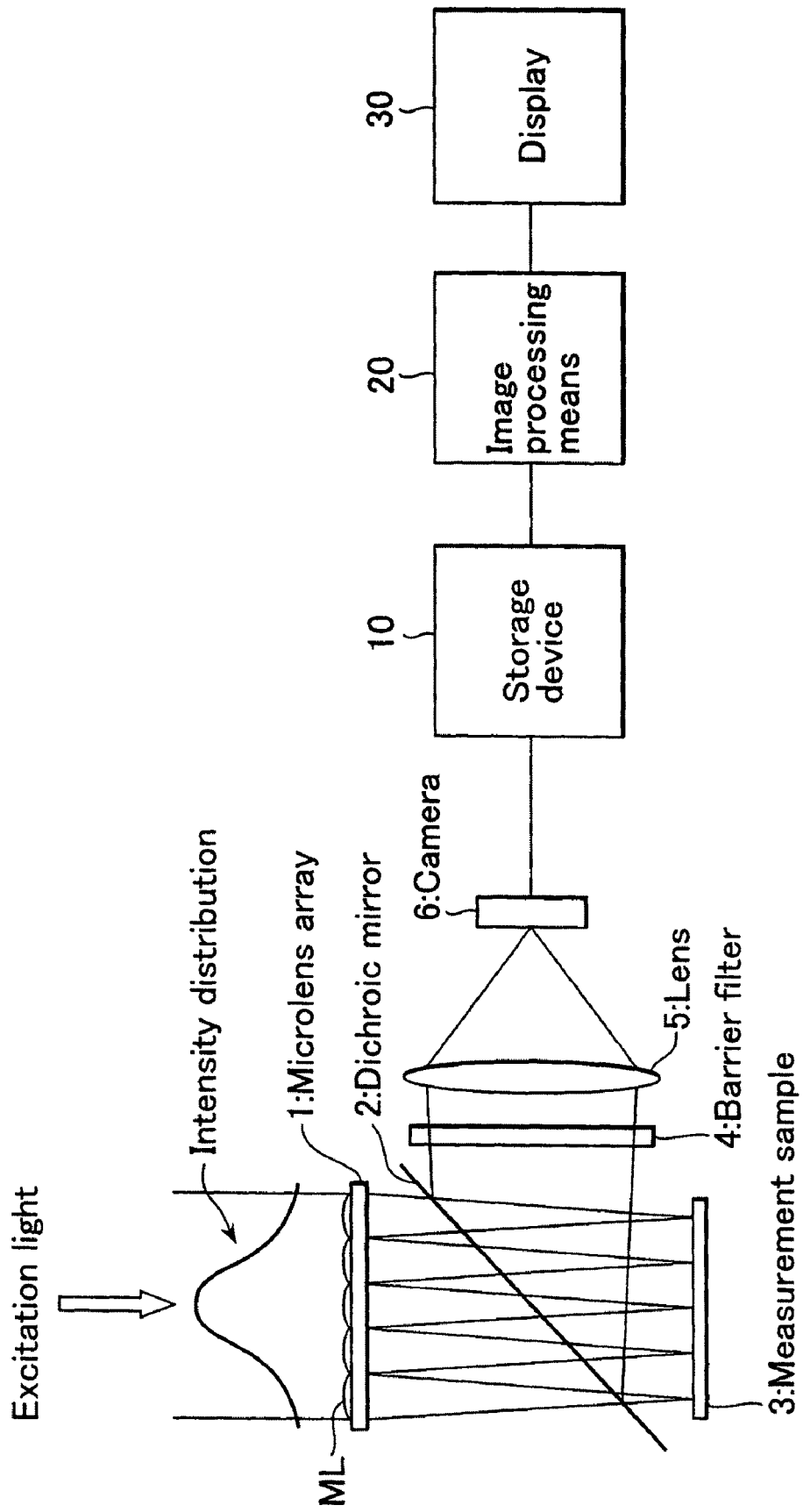
[FIG. 4]

FIG. 4 is a configuration drawing indicating the essential part of an embodiment of a biochip reader for practical use in the method of the present invention. In addition, in FIG. 4, a scan-less type biochip reader is shown, and the same signs as those shown in FIG. 1 are given to the parts identical to those in FIG. 1.

In FIG. 4, storage device 10 stores image data measured with camera 6 included in the capturing means. Image processing means 20 carries out calculation and image processing shown in the above mentioned correction method for the distribution of quantity of light based on image data read from storage device 10. The corrected sample image for the measurement sample obtained is displayed in display 30.

In such a configuration, first fluorescence measurement is done initially by mounting a uniform fluorescent plate in the position of measurement sample 3 and image data of reference quantity of light distribution image "a" obtained with the capturing means, that is, camera 6, is stored in storage device 10.

Next, measurement sample 3 is mounted in lieu of the uniform fluorescent plate and the sample image is measured with camera 6 in the same manner, and image data of that measurement sample image "b" is stored in storage device 10.

In image processing means 20, average tone "$a_{Ave}$" of the total pixels of reference quantity of light distribution image "a" read from storage device 10 is determined, and values of each pixel of the original reference quantity of light distribution image "a" are divided by this average tone "$a_{Ave}$" respectively. The result of this division is given as light source intensity correction image "a'". As described above, light source intensity correction image near 1 is obtained. Subsequently, measurement sample image "b" is divided by the above light source intensity correction image "a'" for each corresponding pixel.

Corrected sample image "c", determined as described above, is indicated in display 30.

In addition, the present invention is not restricted to the above embodiment but may be embodied in other specific forms, changes, and versions without departing from the true spirit thereof.

For example, storage device 10 and image processing means 20 may also be made as an integral configuration, not separate ones.

As apparent from the above description, the following effects are obtained according to the present invention:
(1) A light source intensity correction image, in which the average value is made as 1, is obtained by determining the average tone of an image for a uniform fluorescent plate and by dividing the intensities of each pixel by the average tone. Accordingly, a measured image, in which non-uniformity of quantity of light is corrected, can easily be obtained by dividing the measured image by the above light source intensity correction image.
(2) Since a light source intensity correction image, in which the average value is made as 1, is obtained as described above, it is possible to obtain a light source intensity correction image whose total energy does not change, that is, the total quantity of light energy is maintained.
    Further, according to such correction, no pixel values become extremely large or extremely small.
(3) As seen in the circle in the lower left portion of the image shown in FIG. 2C, sites not seen in the image shown in FIG. 2B become easily visible.

What is claimed is:
1. A biochip reader used for reading images of measurement samples by light beam irradiation, comprising:
    a light source which provides a light which excites a uniform fluorescent plate capable of emitting a fluorescent light which forms uniform fluorescent light distribution on said uniform fluorescent plate and excites a biochip having measurement samples capable of emitting fluorescent light,
    a measuring camera which captures (i) images generated from fluorescent light emitted by the uniform fluorescent plate and (ii) images generated from fluorescent light emitted by the measurement samples on the biochip,
    a storage device which stores image data from said measuring camera,
    an image processing means for correcting the distribution of the quantity of fluorescent light on said biochip according to the following formulas:

$$a_i' = a_i \div a_{ave} \quad (I)$$

$$c_i = b_i \div a_i' \quad (II)$$

and,
    a display which displays images processed by said image processing means,
    wherein $a_i'$ represents a fluorescent light source intensity correction image value for each individual pixel of said uniform fluorescent plate, $a_i$ represents the intensity value of each individual pixel of said uniform fluorescent plate generated by measuring the intensity of each individual pixel of said uniform fluorescent plate with said camera, $a_{ave}$ represents an average value of reference quantity of fluorescent light distribution image of said uniform fluorescent plate generated by averaging a plurality of intensity values of fluorescent images of said uniform fluorescent plate, $c_i$ represents a fluorescent light source intensity corrected sample image value for each individual pixel of said biochip, and $b_i$ represents the intensity value of each individual pixel of said measurement samples on said biochip generated by measuring intensity of each individual pixel of said measurement samples on said biochip with said camera, and wherein i represents a number of each individual pixel of said uniform fluorescent plate and of said measurement samples on said biochip, and has a value of 1 to n.

2. The biochip reader in accordance with claim 1, wherein said image processing means determines an absolute quantity of the light provided by the light source.

3. A biochip reader used for reading images of measurement samples by light beam irradiation, comprising:
- a light source which provides a light which excites a uniform fluorescent plate capable of emitting a fluorescent light which forms uniform fluorescent light distribution on said uniform fluorescent plate and excites a biochip having measurement samples capable of emitting fluorescent light,
- a measuring camera which captures (i) images generated from fluorescent light emitted by the uniform fluorescent plate and (ii) images generated from fluorescent light emitted by the measurement samples on the biochip,
- a storage device which stores image data from said measuring camera,
- an image processing means for correcting the distribution of the quantity of fluorescent light on said biochip according to the following formulas:

$$a_i' = (a_i - x) \div (a_{ave} - x) \quad \text{(I)}$$

$$c_i = b_i \div a_i' \quad \text{(II)}$$

and,
- a display which displays images processed by said image processing means, wherein $a_i'$ represents a fluorescent light source intensity correction image value for each individual pixel of said uniform fluorescent plate, $a_i$ represents the intensity value of each individual pixel of said uniform fluorescent plate generated by measuring the intensity of each individual pixel of said uniform fluorescent plate with said camera, $a_{ave}$ represents an average value of reference quantity of fluorescent light distribution image of said uniform fluorescent plate generated by averaging a plurality of intensity values of fluorescent images of said uniform fluorescent plate, $c_i$ represents a fluorescent light source intensity corrected sample image value for each individual pixel of said biochip, $b_i$ represents the intensity value of each individual pixel of said measurement samples on said biochip generated by measuring intensity of each individual pixel of said measurement samples on said biochip with said camera, and x represents an optical system offset of said measuring camera, and wherein i represents a number of each individual pixel of said uniform fluorescent plate and of said measurement samples on said biochip, and has a value of 1 to n.

4. The biochip reader in accordance with claim 3, wherein said image processing means determines an absolute quantity of the light provided by the light source.

* * * * *